United States Patent [19]

Goodman et al.

[11] 4,283,489

[45] Aug. 11, 1981

[54] PURIFICATION OF NUCLEOTIDE SEQUENCES SUITABLE FOR EXPRESSION IN BACTERIA

[75] Inventors: Howard M. Goodman, Seeburg; John Shine; Peter Horst, both of San Francisco, all of Calif.

[73] Assignee: The Regents of the University of California, San Francisco, Calif.

[21] Appl. No.: 97,049

[22] Filed: Nov. 23, 1979

Related U.S. Application Data

[62] Division of Ser. No. 836,218, Sep. 23, 1977, abandoned.

[51] Int. Cl.³ .............................................. C12Q 1/68
[52] U.S. Cl. .......................................... 435/6; 435/89; 435/91
[58] Field of Search ................................ 435/6, 89, 91

[56] References Cited

U.S. PATENT DOCUMENTS 4,080,261  3/1978  Shibata et al.

OTHER PUBLICATIONS

Panet et al., Biochemistry 12, pp. 5045-5050; 1973.
Roberts, Crit. Rev. Biochem. 4, pp. 123-164; 1976.
Sgarainella et al., Proc. Nat. Acad. Sci. U.S.A., 67, pp. 1468-1475; 1970.
Ullrich et al., Science 196, pp. 1313-1319; 1977.
Maniatis et al., Biochemistry 14, pp. 3787-3794; 1974.
Maxam et al., Proc. Nat. Acad. Sci. U.S.A. 74, pp. 560-564; 1977.
Middleton et al., Journal of Nirology 10, pp. 42-50; 1972.
Modrick et al., J. Biol. Chem. 245, pp. 3626-3631; 1972.
Efstratiadis et al., Cell; 4, pp. 367-378; 1975.
Glisin et al., Biochemistry 13, pp. 2633-2637; 1974.
Horiuchi et al., Proc. Nat. Acad. Sci. U.S.A. 72, pp. 2555-2558; 1975.
Kacian et al., Methods in Enzymology 29, pp. 150-173; 1974.
Aviv et al., Proc. Nat. Acad. Sci. U.S.A. 69; 1408-1412 (1972).
Cox, Methods In Enzymology; 12B, pp. 120-129; 1968.
Dingman et al., Biochemistry 7, pp. 659-668.
Efstratiadis et al., Cell; 7, pp. 279-288; 1976.

Primary Examiner—Robert J. Warden
Attorney, Agent, or Firm—Keil & Witherspoon

[57] ABSTRACT

A method has been discovered for purifying a specific desired DNA sequence, starting from RNA heterogeneous in length and sequence. The steps of the method include making complementary DNA transcripts of the RNA by means of an enzyme such as reverse transcriptase, subjecting the DNA transcripts to the action of one or more selected restriction endonuclease enzymes, and fractionating the fragments produced by endonuclease action according to their length. By this method it is possible to isolate homogeneous length DNA fragments complementary to RNA sequences present in the original preparation in as low a frequency as two percent. A method is also disclosed for further purifying the homogeneous length fragments and for determining their final purity. Using the disclosed methods, a DNA fragment approximately 550 nucleotides in length coding for a portion of the peptide hormone, human chorionic somatomammotropin, has been purified to greater than 99% purity.

5 Claims, 5 Drawing Figures

PURIFICATION OF NUCLEOTIDE SEQUENCES SUITABLE FOR EXPRESSION IN BACTERIA

The invention described herein was made in the course of work under grants from the Department of Health, Education and Welfare.

This is a division of application Ser. No. 836,218, filed Sept. 23, 1977, now abandoned.

BACKGROUND OF THE INVENTION

Proteins and peptides are synthesized in almost endless variety by living organisms. Many have proven to have medical, agricultural or industrial utility. Some proteins are enzymes, useful as specific catalysts for complex chemical reactions. Others function as hormones, which act to affect the growth or development of an organism or to affect the function of specific tissues in medically significant ways. Specific binding proteins may have commercial significance for the isolation and purification of trace substances and for the removal of contaminating substances. Both proteins and peptides are composed of linear chains of amino acids, the latter term being applied to short, single-chain sequences, the former referring to long-chain and multichain substances. The principles of the present invention apply equally to both proteins and peptides.

Proteins and peptides are generally high molecular weight substances, each having a specific sequence of amino acids. Except for the smaller peptides, chemical synthesis of peptides and proteins is frequently impractical, costly and time consuming, if not impossible. In the majority of instances, in order to make practical use of a desired protein, it must first be isolated from the organism which makes it. Frequently, the desired protein is present only in minuscule amounts. Often, the source organism cannot be obtained in quantities sufficient to provide an adequate amount of the desired protein. Consequently, many potential agricultural, industrial and medical applications for specific proteins are known, but remain undeveloped simply because an adequate supply of the desired protein or peptide does not exist.

Recently developed techniques have made it possible to employ microorganisms, capable of rapid and abundant growth, for the synthesis of commercially useful proteins and peptides, regardless of their source in nature. These techniques make it possible to genetically endow a suitable microorganism with the ability to synthesize a protein or peptide normally made by another organism. The technique makes use of a fundamental relationship which exists in all living organisms between the genetic material, usually DNA, and the proteins synthesized by the organism. This relationship is such that the amino acid sequence of the protein is reflected in the nucleotide sequence of the DNA. There are one or more trinucleotide sequence groups specifically related to each of the twenty amino acids most commonly occuring in proteins. The specific relationship between each given trinucleotide sequence and its corresponding amino acid constitutes the genetic code. The genetic code is believed to be the same or similar for all living organisms. As a consequence, the amino acid sequence of every protein or peptide is reflected by a corresponding nucleotide sequence, according to a well understood relationship. Furthermore, this sequence of nucleotides can, in principle, be translated by any living organism.

In its basic outline, a method of endowing a microorganism with the ability to synthesize a new protein involves three general steps: (1) isolation and purification of the specific gene or nucleotide sequence containing the genetically coded information for the amino acid sequence of the desired protein, (2) recombination of the isolated nucleotide sequence with an appropriate transfer vector, typically the DNA of a bacteriophage or plasmid, and (3) transfer of the vector to the appropriate microorganism and selection of a strain of the recipient microorganism containing the desired genetic information.

A fundamental difficulty encountered in attempts to commercially exploit the above-described general process lies in the first step, the isolation and purification of the desired specific genetic information. DNA exists in all living cells in the form of extremely high molecular weight chains of nucleotides. A cell may contain more than 10,000 structural genes, coding for the amino acid sequences of over 10,000 specific proteins, each gene having a sequence many hundreds of nucleotides in length. For the most part, four different nucleotide bases make up all the existing sequences. These are adenine (A), guanine (G), cytosine (C), and thymine (T). The long sequences comprising the structural genes of specific proteins are consequently very similar in overall chemical composition and physical properties. The separation of one such sequence from the plethora of other sequences present in isolated DNA cannot ordinarily be accomplished by conventional physical and chemical preparative methods.

Two general methods have been used in the prior art to accomplish step (1) in the above-described general procedure. The first method is sometimes referred to as the shotgun technique. The DNA of an organism is fragmented into segments generally longer than the desired nucleotide sequence. Step (1) of the above-described process is essentially by-passed. The DNA fragments are immediately recombined with the desired vector, without prior purification of specific sequences. Optionally, a crude fractionation step may be interposed. The selection techniques of microbial genetics are relied upon to select, from among all the possibilities, a strain of microorganisms containing the desired genetic information. The shotgun procedure suffers from two major disadvantages. Most importantly, the procedure can result in the transfer of hundreds of unknown genes into recipient microorganisms, so that during the experiment, new strains are created, having unknown genetic capabilities. Therefore, the use of such a procedure could create a hazard for laboratory workers and for the environment. A second disadvantage of the shotgun method is that it is extremely inefficient for the production of the desired strain, and is dependent upon the use of a selection technique having sufficient resolution to compensate for the lack of fractionation in the first step.

The second general method takes advantage of the fact that the total genetic information in a cell is seldom, if ever, expressed at any given time. In particular, the differentiated tissues of higher organisms may be synthesizing only a minor proportion of the proteins which the organism is capable of making. In extreme cases, such cells may be synthesizing predominantly one protein. In such extreme cases, it has been possible to isolate the nucleotide sequence coding for the protein in question by isolating the corresponding messenger RNA from the appropriate cells.

Messenger RNA functions in the process of converting the nucleotide sequence information of DNA into the amino acid sequence structure of a protein. In the first step of this process, termed transcription, a local segment of DNA having a nucleotide sequence which specifies a protein to be made, is first copied into RNA. RNA is a polynucleotide similar to DNA except that ribose is substituted for deoxyribose and uracil is used in place of thymine. The nucleotide bases in RNA are capable of entering into the same kind of base pairing relationships that are known to exist between the complementary strains of DNA. A and U (T) are complementary, and G and C are complementary. The RNA transcript of a DNA nucleotide sequence will be complementary to the copied sequence. Such RNA is termed messenger RNA (mRNA) because of its status as intermediary between the genetic apparatus of the cell and its protein synthesizing apparatus. Generally, the only mRNA sequences present in the cell at any given time are those which correspond to proteins being actively synthesized at that time. Therefore, a differentiated cell whose function is devoted primarily to the synthesis of a single protein will contain primarily the RNA species corresponding to that protein. In those instances where it is feasible, the isolation and purification of the appropriate nucleotide sequence coding for a given protein can be accomplished by taking advantage of the specialized synthesis of such protein in differentiated cells.

A major disadvantage of the foregoing procedure is that it is applicable only in the relatively rare instances where cells can be found engaged in synthesizing primarily a single protein. The majority of proteins of commercial interest are not synthesized in such a specialized way. The desired proteins may be one of a hundred or so different proteins being produced by the cells of a tissue or organism at a given time. Nevertheless, the mRNA isolation technique is potentially useful since the set of RNA species present in the cell usually represents only a fraction of the total sequences existing in the DNA, and thus provides an initial purification. In order to take advantage of such purification, however, a method is needed whereby sequences present in low frequencies, such as a few percent, can be isolated in high purity.

The present invention provides a process whereby nucleotide sequences can be isolated and purified even when present at a frequency as low as 2% of a heterogeneous population of mRNA sequences. Furthermore, the method may be combined with known methods of fractionating mRNA to isolate and purify sequences present in even lower frequency in the total RNA population as initially isolated. The method is generally applicable to mRNA species extracted from virtually any organism and is therefore expected to provide a powerful basic tool for the ultimate production of proteins of commercial and research interest, in useful quantities.

The process of the present invention takes advantage of certain structural features of mRNA and DNA, and makes use of certain enzyme catalyzed reactions. The nature of these reactions and structural details as they are understood in the prior art are described herewith. The symbols and abbreviations used herein are set forth in the following table:

| | |
|---|---|
| DNA-deoxyribonucleic acid | A-Adenine |
| RNA-ribonucleic acid | T-Thymine |
| cDNA-complementary DNA (enzymatically synthesized from a mRNA sequence) | G-Guanine |
| | C-Cytosine |
| | U-Uracil |
| mRNA-messenger RNA | Tris-2-Amino-2-hydroxyethyl-1,3-propanediol |
| dATP-deoxyadenosine triphosphate | |
| dGTP-deoxyguanosine triphosphate | EDTA-ethylenediamine tetraacetic acid |
| dCTP-deoxycytidine triphosphate | |
| HCS-Human Chorionic Somatomammotropin | ATP-adenosine triphosphate |
| | dTTP-thymidine triphosphate |
| TCA-Trichloroacetic acid | |

In its native configuration, DNA exists in the form of paired linear polynucleotide strands. The complementary base pairing relationships described above exist between the paired strands such that each nucleotide base of one strand exists opposite its complement on the other strand. The entire sequence of one strand is mirrored by a complementary sequence on the other strand. If the strands are separated, it is possible to synthesize a new partner strand, starting from the appropriate precursor monomers. The sequence of addition of the monomers starting from one end is determined by, and complementary to, the sequence of the original intact polynucleotide strand, which thus serves as a template for the synthesis of its complementary partner. The synthesis of mRNA corresponding to a specific nucleotide sequence of DNA is understood to follow the same basic principle. Therefore a specific mRNA molecule will have a sequence complementary to one strand of DNA and identical to the sequence of the opposite DNA strand, in the region transcribed. Enzymic mechanisms exist within living cells which permit the selective transcription of a particular DNA segment containing the nucleotide sequence for a particular protein. Consequently, isolating the mRNA which contains the nucleotide sequence coding for the amino acid sequence of a particular protein is equivalent to the isolation of the same sequence, or gene, from the DNA itself. If the mRNA is retranscribed to form DNA complementary thereto (cDNA), the exact DNA sequence is thereby reconstituted and can, by appropriate techniques, be inserted into the genetic material of another organism. The two complementary versions of a given sequence are therefore inter-convertible, and functionally equivalent to each other.

The nucleotide subunits of DNA and RNA are linked together by phosphodiester bonds between the 5' position of one nucleotide sugar and the 3' position of its next neighbor. Reiteration of such linkages produces a linear polynucleotide which has polarity in the sense that one end can be distinguished from the other. The 3' end may have a free 3'-hydroxyl, or the hydroxyl may be substituted with a phosphate or a more complex structure. The same is true of the 5' end. In eucaryotic organisms, i.e., those having a defined nucleus and mitotic apparatus, the synthesis of functional mRNA usually includes the addition of polyadenylic acid to the 3' end of the mRNA. Messenger RNA can therefore be separated from other classes of RNA isolated from an eucaryotic organism by column chromatograpy on cellulose to which is attached polythymidylic acid. See Aviv, H., and Leder, P., *Proc. Nat. Acad. Sci. USA* 69, 1408 (1972) Other chromatographic methods, exploiting the base-pairing affinity of poly A for chromatographic packing materials containing oligo, dT, poly U, or combinations of poly T and poly U, for example, poly U-Sepharose, are likewise suitable.

Reverse transcriptase catalyzes the synthesis of DNA complementary to an RNA template strand in the presence of the RNA template, a primer which may be any complementary oligo or polynucleotide having a 3'-hydroxyl, and the four deoxynucleotide triphosphates, dATP, dGTP, dCTP, and dTTP. The reaction is initiated by the non-covalent association of the oligodeoxynucleotide primer near the 3' end of mRNA followed by stepwise addition of the appropriate deoxynucleotides, as determined by base pairing relationships with the mRNA nucleotide sequence, to the 3' end of the growing chain. The product molecule may be described as a hairpin structure in which the original RNA is paired by hydrogen bonding with a complementary strand of DNA partly folded back upon itself at one end. The DNA and RNA strands are not covalently joined to each other. Reverse transcriptase is also capable of catalyzing a similar reaction using a single-stranded DNA template, in which case the resulting product is a double-stranded DNA hairpin having a loop of single-stranded DNA joining one set of ends. See Aviv, H. and Leder, P., *Proc. Natl. Acad. Sci. USA* 69, 1408 (1972) and Efstratiadis, A., Kafatos, F. C., Maxam, A.M., and Maniatis, T., *Cell* 7, 279 (1976).

Restriction endonucleases are enzymes capable of hydrolyzing phosphodiester bonds in DNA, thereby creating a break in the continuity of the DNA strand. If the DNA is in the form of a closed loop, the loop is converted to a linear structure. The principal feature of a restriction enzyme is that its hydrolytic action is exerted only at a point where a specific nucleotide sequence occurs. Such a sequence is termed the restriction site for the restriction endonuclease. Restriction endonucleases from a variety of sources have been isolated and characterized in terms of the nucleotide sequence of their restriction sites. When acting on double-stranded DNA, some restriction endonucleases hydrolyze the phosphodiester bonds on both strands at the same point, producing blunt ends. Others catalyze hydrolysis of bonds separated by a few nucleotides from each other, producing free single-stranded regions at each end of the cleaved molecule. Such single-stranded ends are self-complementary, hence cohesive, and may be used to rejoin the hydrolyzed DNA. Since any DNA susceptible to cleavage by such an enzyme must contain the same recognition site, the same cohesive ends will be produced, so that it is possible to join heterogeneous sequences of DNA which have been treated with restriction endonuclease to other sequences similarly treated. See Roberts, R. J. *Crit. Rev. Biochem.* 4, 123 (1976).

It has been observed that restriction sites for a given enzyme are relatively rare and are nonuniformly distributed. Whether a specific restriction site exists within a given segment is a matter which must be empirically determined. However, there is a large nd growing number of restriction endonucleases, isolated from a variety of sources with varied site specificity, so that there is a reasonable probability that a given segment of a thousand nucleotides will contain one or more restriction sites.

For general background see Watson, J. D., *The Molecular Biology of the Gene*, 3d Ed., Benjamin, Menlo Park, California, (1976); Davidson, J. N., *The Biochemistry of the Nucleic Acids*, 8th Ed., Revised by Adams, R. L. P., Burdon, R. H., Campbell, A. M. and Smellie, R. M. S., Academic Press, New York, (1976); and Hayes, W., "The Genetics of Bacteria and Their Viruses", *Studies in Basic Genetics and Molecular Biology*, 2d Ed., Blackwell Scientific Publ., Oxford (1968).

SUMMARY OF THE INVENTION

A novel purification procedure for cDNA of desired nucleotide sequence complementary to an individual mRNA species is disclosed. The method employs restriction endonuclease cleavage of cDNA transcribed from a complex mixture of mRNA. The method does not require any extensive purification of RNA but instead makes use of transcription of RNA into cDNA, the sequence specific fragmentation of this cDNA with one or two restriction endoncleases, and the fractionation of the cDNA restriction fragments on the basis of their length. The use of restriction endonucleases eliminates size heterogeneity and produces homogeneous length DNA fragments from any cDNA species which contains at least two restriction sites. From the initially heterogeneous population of cDNA transcripts, uniform size fragments of desired sequence are produced. The fragments may be several hundred nucleotides in length and may in some instances include the entire structural gene for the desired protein. The length of the fragments depends on the number of nucleotides separating the restriction sites and will usually be different for different regions of DNA. Fractionation by length enables purification of a homogeneous population of fragments having the desired sequence. The fragments will be homogeneous in size and highly pure in terms of nucleotide sequence. Current separation and analysis methods enable the isoltion of such fragments from a corresponding mRNA species representing at least 2% of the mass of the RNA transcribed. The use of prior art RNA fractionation methods to prepurify the mRNA before transcription will result in lowering the actual lower limit of detection to less than 2% of the total mRNA isolated from the organism.

Specific sequences purified by the procedure outlined above may be further purified by a second specific cleavage with a restriction endonuclease capable of cleaving the desired sequence at an internal site. This cleavage results in formation of two sub-fragments of the desired sequence, separable on the basis of their length. The sub-fragments are separated from uncleaved and specifically cleaved contaminating sequences having substantially the same original size. The method is founded upon the rarity and randomness of placement of restriction endonuclease recognition sites, which results in an extremely low probability that a contaminant having the same original length will be cleaved by the same enzyme to yield fragments having the same length as those yielded by the desired sequence. After separation from the contaminants, the sub-fragments of the desired sequence may be rejoined using techniques known in the art, to reconstitute the original sequence. The two sub-fragments must be prevented from joining together in the reverse order of their original sequence. A method is disclosed whereby the sub-fragments can only join to each other in the proper order.

Variations of the above-recited methods may be used in combination with appropriate labelling techniques to obtain accurate, quantitative measurements of the purity of the isolated sequences. The combined techniques have been applied to produce a known nucleotide sequence with greater than 99% purity.

DETAILED DESCRIPTION OF INVENTION

The method of the present invention employs as starting material polyadenylated, crude or partially purified messenger RNA, which may be heterogeneous in sequence and in molecular size. The selectivity of the procedure is enhanced by any method which results in an enrichment of the desired mRNA in the heterodisperse population of mRNA isolated. Any such prepurification method may be employed in conjunction with the method of the present invention, provided the method does not introduce endonucleolytic cleavage of the mRNA. An important initial consideration is the selection of an appropriate source tissue for the desired mRNA. Often, this choice will be dictated by the fact that the protein ultimately to be produced is only made by a certain specialized tissue of a differentiated organism. Such is the case, for example, with the peptide hormones, such as growth hormone or HCS. In other cases, it will be found that a variety of cell types or microbial species can serve as a source of the desired mRNA. In those cases, some preliminary experimentation will be necessary in order to determine the optimal source. Frequently, it will be found that the proportion of desired mRNA can be increased by taking advantage of cellular responses to environmental stimuli. For example, treatment with a hormone may cause increased production of the desired mRNA. Other techniques include growth at a particular temperature and exposure to a specific nutrient or other chemical substance.

Prepurification to enrich for desired mRNA sequences may also be carried out using conventional methods for fractionating RNA, after its isolation from the cell. Any technique which does not result in degradation of the RNA may be employed. The techniques of preparative sedimentation in a sucrose gradient and gel electrophoresis are especially suitable.

The mRNA must be isolated from the source cells under conditions which preclude degradation of the mRNA. The action of RNase enzymes is particularly to be avoided because these enzymes are capable of hydrolytic cleavage of the RNA nucleotide sequence. The hydrolysis of one bond in the sequence results in disruption of that sequence and loss of the RNA fragment containing the original 5' end of the sequence. A suitable method for inhibiting RNase during extraction from cells is disclosed in U.S. application Ser. No. 801,343. The method involves the use of 4 M guanidinium thiocyanate and 1 M mercaptoethanol during the cell disruption step. In addition, a low temperature and a pH near 5.0 are helpful in further reducing RNase degradation of the isolated RNA.

Prior to application of the method of the present invention, mRNA must be prepared essentially free of contaminating protein, DNA, polysaccharides and lipids. Standard methods are well known in the art for accomplishing such purification. RNA thus isolated contains non-messenger as well as messenger RNA. A convenient method for separating the mRNA of eucaryotes is chromatography on columns of oligo-dT cellulose, or other oligonucleotide-substituted column material such as poly U-Sepharose, taking advantage of the hydrogen bonding specificity conferred by the presence of polyadenylic acid on the 3' end of eucaryotic mRNA.

The initial step in the process of the present invention is the formation of DNA complementary to the isolated heterogeneous sequences of mRNA. The enzyme of choice for this reaction is reverse transcriptase, although in principle any enzyme capable of forming a faithful complementary DNA copy of the mRNA template could be used. The reaction may be carried out under conditions described in the prior art, using mRNA as a template and a mixture of the four deoxynucleoside triphosphates dATP, dGTP, dCTP and dTTP, as precursors for the DNA strand. It is convenient to provide that one of the deoxynucleoside triphosphates be labeled with a radioisotope, for example $^{32}p$ in the alpha position, in order to monitor the course of the reaction, to provide a tag for recovering the product after separation procedures such as chromatography and electrophoresis, and for the purpose of making quantitative estimates of recovery. See Efstratiadis, A., et al., supra.

The cDNA transcript produced by the reverse transcriptase reaction is indeterminate at both the 5' end and the 3' end. The variability of sequence at the 5' end is thought to be due to the fact that the oligo-dT primer used to initiate synthesis is capable of binding at a variety of loci along the polyadenylated region of the mRNA. Synthesis of the cDNA transcript begins at an indeterminate point in the poly-A region, and a variable length of poly-A region is transcribed depending on the initial binding site of the oligo-dT primer. It is possible to avoid this indeterminacy by the use of a primer containing, in addition to an oligo-dT tract, one or two nucleotides of the RNA sequence itself, thereby producing a primer which will have a preferred and defined binding site for initiating the transcription reaction.

The indeterminacy at the 3' end of the cDNA transcript is due to a variety of factors affecting the reverse transcriptase reaction, and to the possibility of partial degradation of the RNA template. The isolation of specific cDNA transcripts of maximal length is greatly facilitated if conditions for the reverse transcriptase reaction are chosen which not only favor full length synthesis but also repress the synthesis of small DNA chains. Preferred reaction conditions for avian myeloblastosis reverse transcriptase are given in the examples section. The specific parameters which may be varied to provide maximal production of long-chain DNA transcripts of high fidelity are reaction temperature, salt concentration, amount of enzyme, concentration of primer relative to template, and reaction time.

The conditions of temperature and salt concentration are chosen so as to optimize specific base pairing between the oligo-dT primer and the polyadenylated portion of the RNA template. Under properly chosen conditions, the primer will be able to bind at the polyadenylated region of the RNA template, but non-specific initiation due to primer binding at other locations on the template, such as short, A-rich sequences, will be substantially prevented. The effects of temperature and salt are interdependent. Higher temperatures and lower salt concentrations decrease the stability of specific base-pairing interactions. The reaction time is kept as short as possible, in order to prevent non-specific initiations and to minimize the opportunity for degradation. Reaction times are interrelated with temperature, lower temperatures requiring longer reaction times. At 42° C., reactions ranging from 1 min. to 10 minutes are suitable. The primer should be present in 50 to 500-fold molar excess over the RNA template and the enzyme should be present in similar molar excess over the RNA template. The use of excess enzyme and primer enhances initiation and cDNA chain growth so that long-chain cDNA transcripts are produced efficiently within the confines of the short incubation times.

In many cases, it will be possible to carry out the remainder of the process of the present invention using single-stranded cDNA sequences transcribed from mRNA. However, as discussed below, there may be instances in which the desired restriction enzyme is one which acts only on double-stranded DNA. In these cases, the cDNA prepared as described above may be used as a template for the synthesis of double-stranded DNA, using reverse transcriptase and a nuclease capable of hydrolyzing single-stranded DNA. Methods for preparing double-stranded DNA in this manner have been described in the prior art. See, for example, Ullrich, A., Shine, J., Chirgwin, J., Pictet, R., Tischer, E., Rutter, W. J. and Goodman, H. M., *Science* 196, 1313 (1977).

Heterogeneous cDNA, prepared by transcription of heterogeneous mRNA sequences, is then treated with one or two restriction endonucleases. The choice of endonuclease to be used depends in the first instance upon a prior determination that recognition sites for the enzyme exist in the sequence of the cDNA to be isolated. The method depends upon the existence of two such sites. If the sites are identical, a single enzyme will be sufficient. The desired sequence will be cleaved at both sites, eliminating size heterogeniety as far as the desired cDNA sequence is concerned, and creating a population of molecules, termed fragments, containing the desired sequence and homogeneous in length. If the restriction sites are different, two enzymes will be required in order to produce the desired homogeneous length fragments.

The choice of restriction enzyme(s) capable of producing an optimal length nucleotide sequence fragment coding for all or part of the desired protein must be made empirically. If the amino acid sequence of the desired protein is known, it is possible to compare the nucleotide sequence of uniform length nucleotide fragments produced by restriction endonuclease cleavage with the amino acid sequence for which it codes, using the known relationships of the genetic code common to all forms of life. A complete amino acid sequence for the desired protein is not necessary, however, since a reasonably accurate identification may be made on the basis of a partial sequence. Where the amino acid sequence of the desired protein is not known, the uniform length polynucleotides produced by restriction endonuclease cleavage may be used as probes capable of selectively hybridizing with full length mRNA capable of directing the synthesis of the desired protein in an appropriate in vitro protein synthesizing system. Alternatively, the mRNA may be purified by affinity chromatography. Other techniques which may be suggested to those skilled in the art will be appropriate for this purpose.

The number of restriction enzymes suitable for use depends upon whether single-stranded or double-stranded cDNA is used. The preferred enzymes are those capable of acting on single-stranded DNA, which is the immediate reaction product of mRNA transcription. The number of restriction enzymes now known to be capable of acting on single-stranded DNA is limited. The enzymes HaeIII, HhaI and Hin(f)I are presently known to be suitable. In addition, the enzyme MboII may act on single-stranded DNA. Where further study reveals that other restriction enzymes can act on single-stranded DNA, such other enzymes may appropriately be included in the list of preferred enzymes. Additional suitable enzymes include those specified for double-stranded cDNA. Such enzymes are not preferred since additional reactions are required in order to produce double-stranded cDNA, providing increased opportunities for the loss of longer sequences and for other losses due to incomplete recovery. The use of double-stranded cDNA presents the additional technical disadvantage that subsequent sequence analysis is more complex and laborious. For these reasons, single-stranded cDNA is preferred, but the use of double-stranded DNA is feasible.

The cDNA prepared for restriction endonuclease treatment may be radioactively labeled so that it may be detected after subsequent separation steps. A preferred technique is to incorporate a radioactive label such as 32P in the alpha position of one of the four deoxynucleoside triphosphate precursors. Highest activity is obtained when the concentration of radioactive precursor is high relative to the concentration of the non-radioactive form. However, the total concentration of any deoxynucleotide triphosphate should be greater than 30 $\mu$M, in order to maximize the length of cDNA obtained in the reverse transcriptase reaction. See Efstratiadis, A., Maniatis, T., Kafatos, F. C., Jeffrey, A., and Vournakis, J. N., *Cell* 4, 367 (1975). For the purpose of determining the nucleotide sequence of cDNA, the 5' ends may be conveniently labeled with 32P in a reaction catalyzed by the enzyme polynucleotide kinase. See Maxam, A. M. and Gilbert, W., *Proc. Natl. Acad. Sci USA* 74, 560 (1977).

Fragments which have been produced by the action of a restriction enzyme or combination of two restriction enzymes may be separated from each other and from heterodisperse sequences lacking recognition sites by any appropriate technique capable of separating polynucleotides on the basis of differences in length. Such methods include a variety of electrophoretic techniques and sedimentation techniques using an ultracentrifuge. Gel electrophoresis is preferred because it provides the best resolution on the basis of polynucleotide length. In addition, the method readily permits quantitative recovery of separated materials. Convenient gel electrophoresis methods have been described by Dingman, C. W., and Peacock, A. C., *Biochemistry* 7, 659 (1968), and by Maniatis, T., Jeffrey, A. and van de Sande, H., *Biochemistry* 14, 3787 (1975).

Prior to restriction endonuclease treatment, cDNA transcripts obtained from most sources will be found to be heterodisperse in length. By the action of a properly chosen restriction endonuclease, or pair of endonucleases, polynucleotide chains containing the desired sequence will be cleaved at the respective restriction sites to yield polynucleotide fragments of uniform length. Upon gel electrophoresis, these will be observed to form a distinct band. Depending on the presence or absence of restriction sites on other sequences, other discrete bands may be formed as well, which will most likely be of different length than that of the desired sequence. Therefore, as a consequence of restriction endonuclease action, the gel electrophoresis pattern will reveal the appearance of one or more discrete bands, while the remainder of the cDNA will continue to be heterodisperse. In the case where the desired cDNA sequence comprises the majority of the polynucleotide species present, the electrophoresis pattern will reveal that most of the cDNA is present in a discrete band.

Although it is unlikely that two different sequences will be cleaved by restriction enzymes to yield fragments of essentially similar length, a method for determining the purity of the defined length fragments is desirable. Sequence analysis of the electrophoresis band may be used to detect impurities representing 10% or more of the material in the band. A method for detecting lower levels of impurities has been developed, as part of the present invention, founded upon the same general principles applied in the initial isolation method. The method also permits the further purification of the desired sequence. The method requires that the desired nucleotide sequence fragment contain a recognition site for a restriction endonuclease not employed in the initial isolation. Treatment of polynucleotide material, eluted from a gel electrophoresis band, with a restriction endonuclease capable of acting internally upon the desired sequence will result in cleavage of the desired sequence into two sub-fragments, most probably of unequal length. These sub-fragments upon electrophoresis will form two discrete bands at positions corresponding to their respective lengths, the sum of which will equal the length of the polynucleotide prior to cleavage. Contaminants in the original band that are not susceptible to the restriction enzyme may be expected to migrate to the original position. Contaminants containing one or more recognition sites for the enzyme may be expected to yield two or more sub-fragments. Since the distribution of recognition sites is believed to be essentially random, the probability that a contaminant will also yield sub-fragments of the same size as those of the fragment of desired sequence is extremely low. The amount of material present in any band of radioactively labeled polynucleotide can be determined by quantitative measurement of the amount of radioactivity present in each band, or by any other appropriate method. A quantitative measure of the purity of the fragments of desired sequence can be obtained by comparing the relative amounts of material present in those bands representing sub-fragments of the desired sequence with the total amount of material.

Following the foregoing separation, the desired sequence may be reconstituted. The enzyme DNA ligase, which catalyzes the end-to-end joining of DNA fragments, may be employed for this purpose. The gel electrophoresis bands representing the sub-fragments of the desired sequence may be separately eluted and combined in the presence of DNA ligase, under the appropriate conditions. See Sgaramella, V., Van de Sande, J. H., and Khorana, H. G., *Proc. Natl. Acad. Sci USA* 67, 1468 (1970). Where the sequences to be joined are not blunt-ended, the ligase obtained from *E. Coli* may be used, Modrich, P., and Lehman, I. R., *J. Biol. Chem.* 245, 3626 (1970).

The efficiency of reconstituting the original sequence from sub-fragments produced by restriction endonuclease treatment will be greatly enhanced by the use of a method for preventing reconstitution in improper sequence. This unwanted result is prevented by treatment of the homogeneous length cDNA fragment of desired sequence with an agent capable of removing the 5'-terminal phosphate groups on the cDNA prior to cleavage of the homogeneous cDNA with a restriction endonuclease. The enzyme, alkaline phosphatase, is preferred. The 5'-terminal phosphate groups are a structural prerequisite for the subsequent joining action of DNA ligase used to reconstitute the cleaved sub-fragments. Therefore, ends which lack a 5'-terminal phosphate cannot be covalently joined. The DNA sub-fragments can only be joined at the ends containing a 5'-phosphate generated by the restriction endonuclease cleavage performed on the isolated DNA fragments. The method is essentially that described in detail in copending U.S. application Ser. No. 801,343.

The majority of cDNA transcripts, under the conditions employed, are derived from the mRNA region containing the 3'-end of mRNA. The fragments of desired sequence which are isolated are therefore most likely to be near the 3'-end of the mRNA. Such fragments should make it possible to obtain a longer cDNA fragment containing the 5'-end of the mRNA template by specifically priming on the same template with a fragment obtained by restriction endonuclease cleavage. In this way, the above-described method may be used to obtain not only fragments of specific nucleotide sequence related to a desired protein, but also the entire nucleotide sequence coding for the protein of interest.

Using the above-described methods for purification and analysis, a desired nucleotide sequence containing most of the structural gene for human HCS has been isolated and shown to be greater than 99% pure.

BRIEF DESCRIPTION OF THE FIGURES

The accompanying figures and drawing are provided to demonstrate the results obtained in the specific examples illustrating the invention.

EXAMPLE 1

The general procedure for isolating a specific cDNA sequence has been demonstrated by isolating a sequence comprising a portion of the coding region for HCS, extracted from placental tissue.

mRNA Extraction From Placenta

Human term placentas obtained from cesarean section were quick-frozen in liquid nitrogen and stored at $-60°$ C. For extraction of total RNA, 40 g of the frozen placental tissue was broken into small pieces and dissolved with the aid of a blender in 140 ml of freshly prepared 7 M guanidinium-HC1 (Cox, R. A., *Methods in Enzymology* 12, 120 (1968)), 20 mM Tris-HCl pH 7.5, 1 mM EDTA, 1% sarcosyl* at 0° C. After adding 0.5 g CsCl to each ml, the dark brown solution was heated at 65° C. for 5 min, quick-cooled in ice, layered on top of a 5 ml cushion of 5.7 M CsCl, 10 mM Tris-HCl, pH 7.5, 1 mM EDTA in lin$\times 3\frac{1}{2}$ in nitrocellulose tubes and centrifuged in an SW27 rotor (Beckman Instruments Corp., Fullerton, Calif.) at 27,000 rpm for 16 hr at 15° C. (Glisin, V., Crkvenjakov, R., and Ryus, C., *Biochem.* 13, 2633 (1974)). After centrifugation, the tube contents were decanted, the tubes were drained, and the bottom ½ cm containing the clear RNA pellet was cut off with a razor blade. Pellets were transferred into a sterile erlenmeyer flask and dissolved in 20 ml 10 mM Tris-HCl, pH 7.5, 1 mM EDTA, 5% sarcosyl and 5% phenol. The solution was then made 0.1 M in NaCl and vigorously shaken with 40 ml of a 50% phenol-50% chloroform mixture. RNA was precipitated from the aqueous phase with ethanol in the presence of 0.2 M Na-acetate pH 5.5. RNA pellets were washed with 95% ethanol, dried, and dissolved in sterile water. Usually 40 g of placental tissue yielded about 30 mg of RNA from which approximately 300 μg of polyadenylated RNA was obtained after twice chromatographing on oligo-dT cellulose. See Aviv, and Leder, supra.

*Trademark, Ciba-Geigy Corp., Greensboro, N.C.

Synthesis of cDNA

Analytical reactions were performed in 5 μl containing 50 mM Tris-HCl pH 8.3; 0.1 mM EDTA; 7 mM $MgCl_2$; 20 mM KCl; 10 mM β-mercaptoethanol; 40 μM dCTP (50,000 cpm $^{32}P$ per pmole); 500 μM each dCTP, dATP, and dTTP; 100 μg/ml of polyadenylated RNA; 20 μg/ml oligo-$dT_{12-18}$ obtained from Collaborative Research, Waltham, Mass.; and 100 units/ml reverse transcriptase from avian myeloblastosis virus. The enzyme is available from Dr. D. J. Beard, Life Science Incorporated, St. Petersburg, Fla., who produces the enzyme under contract with the National Institutes of Health, by the procedure of Kacian, D. L. and Spiegelman, S., in *Methods in Enzymology* 29, L. Grossman, and K. Moldave, eds., Academic Press, N.Y. (1974), p. 150. Reactions were started by the addition of enzyme at 0° C. and synthesis was for 6 min at 42° C. Under these conditions approximately $10^6$ cpm $^{32}P$ were incorporated into TCA-precipitable material and each μg of RNA yielded about 50 ng of cDNA. To obtain enough cDNA for sequence analysis, the reaction volumes were increased to 100 μl and the dCTP concentration was raised to 250 μM (specific activity of 500 cpm $^{32}P$ per pmole). Under these conditions about 200,000 cpm of $^{32}P$-labeled dCMP were incorporated into cDNA.

Restriction Endonuclease Treatment

For restriction endonuclease digestions the analytical reactions were stopped by the addition of 20 μl of ice-cold water, boiled for 2 min, quick-cooled on ice, and made 7 mM in $MgCl_2$. Aliquots (5 μl, about $2 \times 10^5$ cpm) were digested using an excess amount of restriction endonuclease(s) HaeIII or HhaI or both, for 1 hr at 37° C. HaeIII was prepared according to the method of Middleton, J. H., Edgell, M. H., and Hutchison, C. A. III, *J. Virol.*, 10, 42 (1972). HhaI and HpaII were obtained from New England Bio-Labs, Beverly, Mass. HaeIII is also available from the latter source. The amount of enzyme used was empirically determined to be in excess of the amount needed to completely digest an equivalent amount of restriction-sensitive DNA under identical reaction conditions. Reactions were stopped with 5 μl of 20 mM EDTA, 20% sucrose, 0.05% bromophenolblue, heated to 100° C. for 1 min and then analyzed by polyacrylamide gel electrophoresis. The products were separated on a composite 4.5%-10% polyacrylamide slab gel for 2.5 hr at 150 V in Tris-Borate-EDTA buffer (Dingman, C. W. and Peacock, A. C., supra) and visualized by autoradiography of the dry gel.

Figure 1:
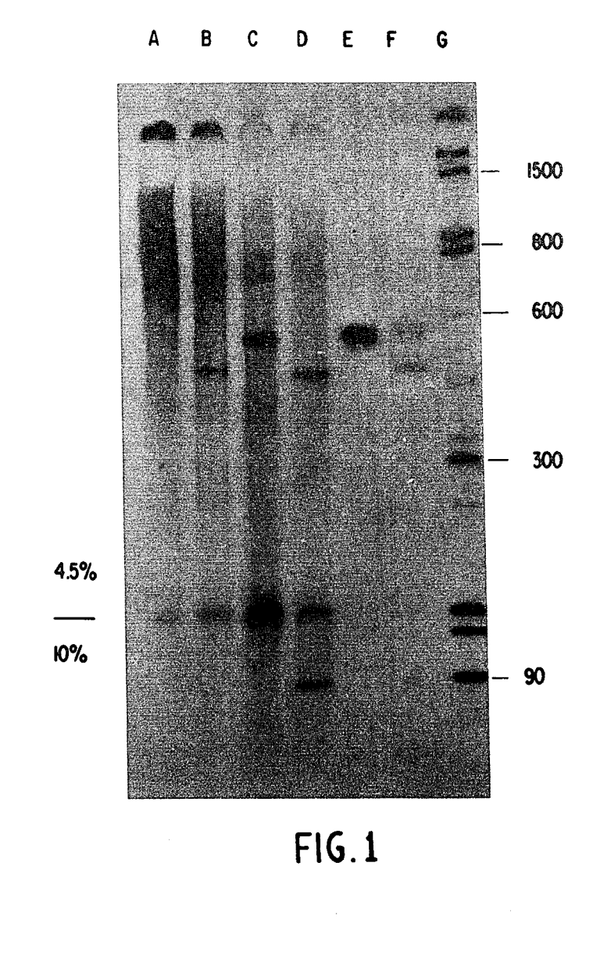
FIG. 1 is an autoradiogram of a series of gel electrophoresis runs of 32P-labeled cDNA, as described in detail in Example 1.

FIG. 1 shows the results of gel electrophoresis and autoradiography of $^{32}P$-labeled cDNA, prepared as described above. The samples were initially spotted at the origin and migrated electrophoretically through 4.5% acrylamide and then through 10% acrylamide. A bar is placed on the left hand side of the figure to indicate the position of the boundary between the two gel regions. Lane A represents the electrophoretic migration of the total cDNA transcript. Lane B shows the migration of HhaI treated cDNA. Lane C shows the migration of HaeIII treated cDNA. Lane D shows the electrophoretic migration of total cDNA treated with both HhaI and HaeIII. Lane E demonstrates the electrophoretic migration of the material isolated from the prominent band in Lane C. Lane F shows electrophoretic migration of isolated material from the prominent band of Lane C after treatment with HhaI. Lane G shows the electrophorectic migration of HaeIII cleaved 5'-$^{32}P$ end-labeled singlestranded phage M13 DNA used as a size standard, according to Horiuchi, K., and Zinder, N. D., *Proc. Nat. Acad. Sci USA* 72, 2555 (1975). The approximate lengths in nucleotides of these DNA fragments are indicated by the numbers on the right.

The result in Lane A demonstrates that the cDNA transcript from term placental mRNA is heterodisperse. Treatment with HhaI, Lane B or HaeIII, Lane C results in the accumulation of polynucleotides of discrete length. The production of such discrete bands indicates the presence, in a heterogeneous population of cDNA transcripts, of at least one sequence present in multiple copies and having two restriction sites for HhaI and HaeIII respectively. Cleavage with HhaI produces a fragment of about 470 nucleotides, and HaeIII digestion produces a fragment of approximately 550 nucleotides in length. Digestion by both enzymes yields three fragments designated A, 90 nucleotides long, B, 460 nucleotides long, and C, approximately 10 nucleotides long. Due to its small size, fragment C migrated off the gel under the conditions used in FIG. 1. The band of material appearing at the interface between 10% and 4.5% gel represents heterogeneous material which was too large to enter the 10% gel and therefore accumulated at the interface. As judged from the simple band pattern of Lane D, fragments A and B seem to originate from the same cDNA molecule. This conclusion was confirmed by elution of the larger HaeIII fragment from the gel, migrating as shown in Lane E, followed by redigestion with HhaI. Such treatment produced two fragments comigrating with the bands released by combined HaeIII and HhaI digestion of the total cDNA, as seen by comparing Lanes D and F. In the total cDNA digest, Lane D, the autoradiographic density, which is a measure of the total radioactivity present in the band, is greater for fragment A than fragment B. Although the reverse may be expected on the basis of size differences. This observation suggests that fragment A is transcribed from a region closer to the 3'-end of the mRNA than is fragment B.

Figure 2:
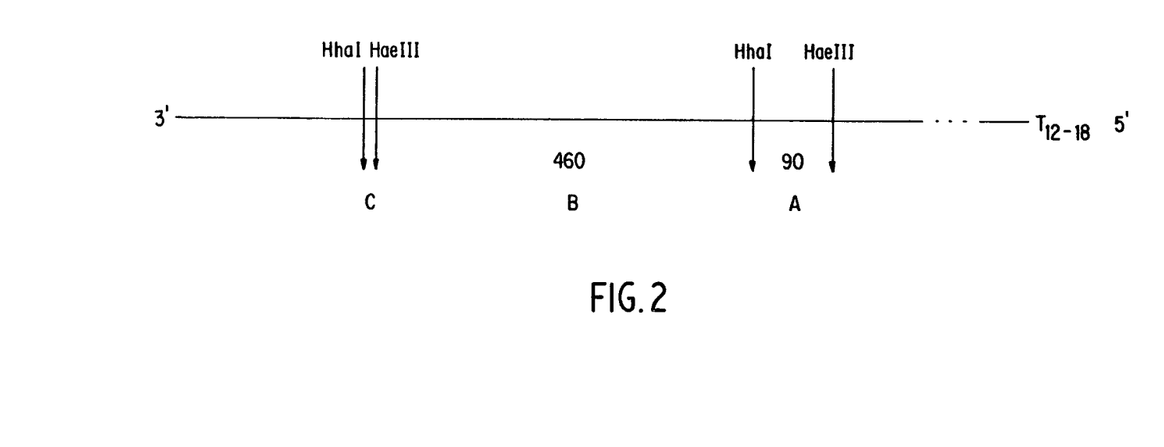
FIG. 2 is a schematic representation of the nucleotide sequence coding for HCS, showing the relative locations of various restriction sites, as described in detail in Example 1.

FIG. 2 is a schematic representation of the cDNA molecule showing the relative locations of the HaeIII and HhaI restriction sites. DNA fragments A and B, derived from the same cDNA molecule, were ordered on the basis of their relative intensity on the autoradiogram shown in FIG. 1, Lane D. The existence of DNA fragment C was inferred from the difference in the electrophoretic mobility of the band appearing in Lane B and Lane D of FIG. 1. The size of DNA fragment A is known exactly from a determination of its nucleotide sequence by the method of Maxam, A. and Gilbert, W., supra. The size of DNA fragment B was determined by comparison with the M13 DNA size markers shown in FIG. 1, Lane G.

The nucleotide sequences of DNA fragment A and a portion of the 5'-end of fragment B were determined by the procedure of Maxam, A. and Gilbert, W., supra. Since the amino acid quence of HCS is known, the nucleotide sequence of the two fragments could be compared with the amino acid sequence, using the known relationships of the genetic code. On the basis of these relationships it was demonstrated that the specific sequences did in fact code for portions of the HCS molecule, and further confirmed the ordering of these fragments shown in FIG. 2.

EXAMPLE 2

The ability of the process of the present invention to purify a desired nucleotide sequence that is a minority proportion of the total population of nucleotide sequences is demonstrated in the following reconstruction experiment. Defined RNA mixtures containing purified rabbit globin RNA and human polyadenylated placental RNA were used as template for reverse transcriptase in the presence of alpha-$^{32}$P dCTP, final specific activity, $10^5$ cpm per pmole. The cDNA products were cleaved with endonuclease HaeIII and the cleavage products were separated on 4.5%–10% composite polyacrylamide slab gel. The cDNA fragments were visualized by autoradiography of the dried gel.

Figure 3:
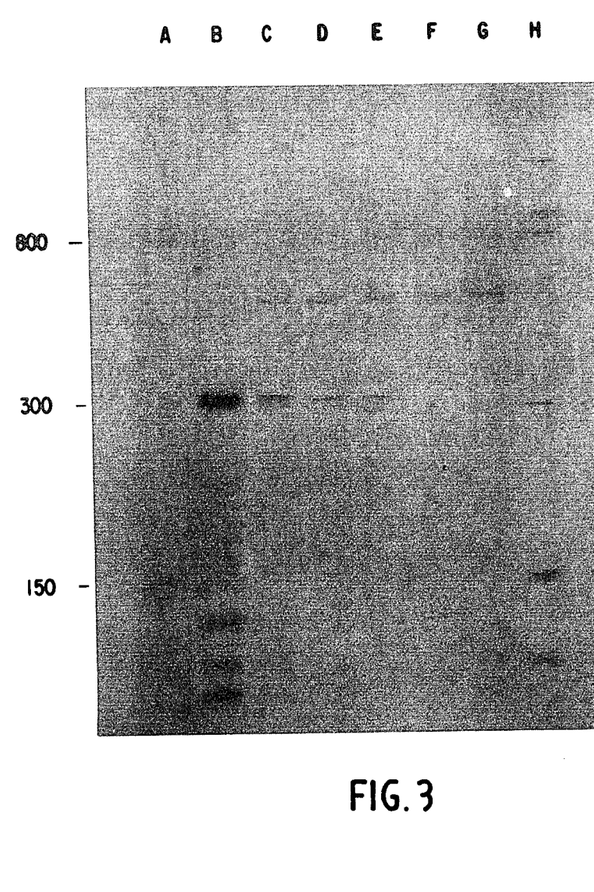
FIG. 3 is an autoradiogram of gel electrophoresis results using 32P-labeled cDNA, as described in detail in Example 2.

FIG. 3 shows the results of the experiments. The gels were run essentially as described in example 1. Size markers prepared by endonuclease HaeIII cleavage of phage M13 DNA and 5'-$^{32}$P end labeling of the fragments thereby produced, were run in lanes A and H. The approximate lengths in nucleotides of these DNA fragments are indicated by the numbers on the left. Lanes B–G show the electrophoresis patterns produced by initiating the foregoing sequence of reactions with mixtures of globin RNA and placental RNA in varying proportions, as shown in the following table.

| Lane | Globin RNA nanograms | Placental RNA nanograms |
|---|---|---|
| B | 300 | 0 |
| C | 60 | 240 |
| D | 30 | 270 |
| E | 15 | 285 |
| F | 7.5 | 292.5 |
| G | 0 | 300 |

It can be seen that a 320 nucleotide long HaeIII fragment is derived from globin cDNA. The globin cDNA transcript can still be detected if globin RNA represents as little as 2–5% of the total RNA. If an RNA species is present as isolated in too low a copy number to be amenable to this mode of analysis, it can be first partially purified by any one of the known RNA purification schemes until it represents about 2–5% of the remaining species mixture.

EXAMPLE 3

The purification of a nucleotide sequence fragment approximately 550 base-pairs in length comprising a portion of the coding region for human HCS is described, together with a method of measuring the purity of the isolated sequence. The purified fragment is demonstrated to be greater than 99% pure.

Purification of Human HCS cDNA

Figure 4:
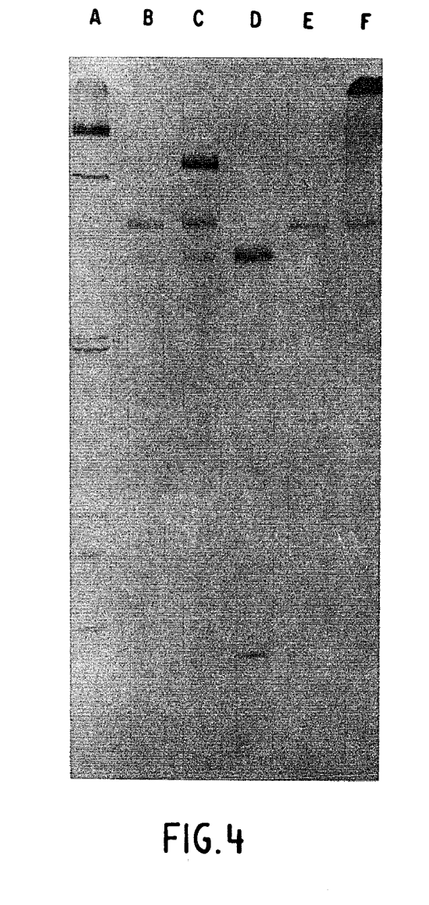
FIGS. 4 and 5 are autoradiograms of gel electrophoresis results using 32P-labeled cDNA, as described in detail in Example 3.

Polyadenylated placental RNA isolated as described in Example 1 was enriched for HCS mRNA by sedimentation in a 5% to 20% (w/v) sucrose gradient at 4° C. in the SW 27 rotor of a Beckman Instruments ultracentrifuge at 25,000 rpm for 16 hours. The 11S-14S region of the gradient was pooled and 100 μg of this RNA used for the synthesis of double-stranded cDNA as described by Ullrich, A., et al., supra. Synthesis of the second strand was stopped by extraction of the reaction mixture with one volume of ethanol at −70° C. Digestion of the cDNA with HaeIII endonuclease was carried out in 50 μl of 6 mM Tris-HCl, pH 7.5, 6 mM MgCl$_2$, 6 mMβ-mercaptoethanol with 2 units of HaeIII enzyme at 37° C. for two hours, following which 0.1 units of bacterial alkaline phosphatase were added and digestion continued at 60° C. for ten minutes. Following extraction with one volume of phenol-chloroform, the DNA was precipitated with two volumes of ethanol −70° C., dissolved in 20 μl of 10 mM Tris-HCl, pH 8, 1 mM EDTA, and subjected to electrophoresis on a 6% (w/v) polyacrylamide gel. FIG. 4(F) shows the electrophoresis pattern of the foregoing reaction mixture, which reveals a prominent band corresponding to a nucleotide sequence approximately 550 base pairs in length. The 550 base pair fragment was excised from the gel, and eluted electrophoretically, with the result shown in FIG. 4(E).

The remaining material corresponding to the 550 base pair fragment shown in FIG. 4(E) was digested with 4 units of HhaI endonuclease in 50 μl of the same buffer used for digestion with HaeIII endonuclease, at 37° C. for 2 hours. Following phenol-chloroform extraction and ethanol precipitation, the digestion products were separated by electrophoresis on a 6% (w/v) polyacrylamide gel. The result is shown in FIG. 4(D).

The two fragments were eluted electrophoretically, combined and rejoined by incubation in 20 μl of 66 mM Tris-HCl, pH 7.6, 6 mM MgCl$_2$, 15 mM dithiothreitol, 1 mM ATP containing 20 μg/ml of T4 DNA ligase at 15° C. for two hours. The reaction mixture was then diluted to 200 μl with 0.1 M NaCl, extracted with 1 volume of phenol-chloroform and the DNA precipitated with 2 volumes of ethanol. After resuspension in 20 μl of 10 mM Tris-HCl, pH 8, 1 mM EDTA, the ligation products were separated by electrophoresis in the 6% (w/v) polyacrylamide gel. The result is shown in FIG. 4(C). It can be seen from the electrophoresis pattern of FIG. 4(C) that the 550 nucleotide fragment was reconstituted by the ligation treatment. The prior treatment with alkaline phosphatase insured that the two HhaI fragments were rejoined in the original sequence relative to each other to reconstitute the 550 nucleotide segment. The additional bands seen in FIG. 4(C) were the result of dimer formation between the HhaI fragments, since dimer formation is not prevented by the alkaline phosphatase treatment.

The reconstituted 550 nucleotide fragment was excised from the gel and eluted electrophoretically. The electrophoresis pattern of the eluted material is shown in FIG. 4(B). FIG. 4(A) represents the electrophoresis pattern of $^{32}$P-labeled HaeIII digest of double-stranded M13 DNA used as a size marker. The electrophoretic analyses were conducted in a 6% (w/v) polyacrylamide gel in 50 mM Tris-borate, pH 8, 1 mM EDTA at 100 volts for two hours. Following electrophoresis, the gel was dried and exposed to Kodak NS2T x-ray film to produce the autoradiograms.

Purity of Reconstituted 550 Nucleotide Fragment of Human HCS cDNA

The isolated reconstituted HCS HaeIII fragment was labeled with $^{32}P$ at its 5' ends using the enzyme polynucleotide kinase obtained from bacteriophage T4-infected *E. coli* by the method of Panet, A., et al., *Biochemistry* 12, 5045 (1973). The fragment was then digested with either HhaI or HpaII in 50 μl of 6 mM Tris-HCl, pH 7.6, 6 mM $MgCl_2$, 6 mM β-mercaptoethanol at 37° C. for two hours. Following extraction with an equal volume of phenolchloroform, the DNA was precipitated with two volumes of ethanol at −70° C., resuspended in 20 μl, 10 mM Tris-HCl, pH 8, 1 mM EDTA and subjected to electrophoresis in a 6% (w/v) polyacrylamide gel. Following electrophoresis, the gel was exposed to x-ray film to visualize the labeled fragments, as described previously.

Figure 5:
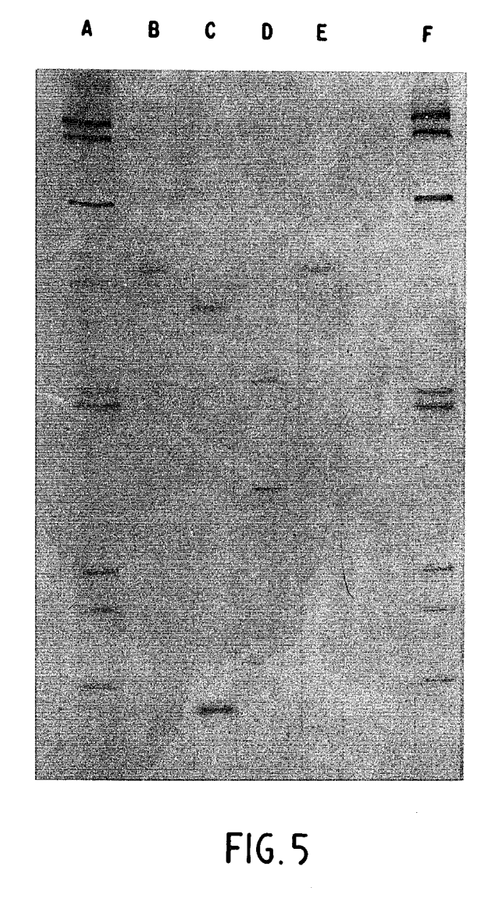

Results are shown in FIG. 5. FIGS. 5(B) and 5(E) represent duplicate runs of the 550 nucleotide fragment prior to restriction enzyme digestion. FIG. 5(C) represents the pattern resulting from HhaI cleavage and FIG. 5(D) represents the pattern resulting from HpaII cleavage.

The purity of the 550 nucleotide fragment was measured by scanning the autoradiogram of the restriction enzyme cleavage products and by quantitation of the distribution of radioactivity in each of the two restriction endonuclease digests. Such measurements reveal that the purified human HCS cDNA reconstituted HaeIII fragment was greater than 99% homogeneous.

GENERAL CONCLUDING REMARKS

The process of the present invention provides for the first time a method of general applicability for purifying desired specific nucleotide sequences. These sequences may be correlated with the production of a specific protein of commercial or medical significance. The disclosed process results in the purification of nucleotide sequences which may be fragments of a larger sequence coding for the desired protein. The present method may be used in combination with known ancillary procedures to produce the entire nucleotide sequence coding for a specific protein.

In addition, a method has been disclosed whereby a nucleotide sequence of specific length, however derived, may be highly purified. A method for measuring the degree of purity of such fragments is also disclosed. By these means, a nucleotide sequence coding for a portion of human HCS has been isolated, purified and shown to be at least 99% pure.

While the invention has been described in connection with specific embodiments thereof, it will be understood that it is capable of further modifications and this application is intended to cover any variations, uses or adaptations of the invention following, in general, the principles of the invention and including such departures from the present disclosure as come within known or customary practice within the art to which the invention pertains or which would be readily apparent to those skilled in said art. With that understanding, the invention is not to be limited except to the extent required by the appended claims.

What is claimed is:

1. A method for measuring the purity of a specific desired nucleotide sequence in a preparation of DNA fragments of essentially homogeneous length containing said nucleotide sequence, there being at least one restriction site within the specific desired nucleotide sequence, comprising the steps of:
   a. subjecting the DNA preparation to the action of a restriction endonuclease capable of catalyzing the hydrolysis of the specific desired nucleotide sequence at the restriction site within the sequence, in order to produce identifiable sub-fragments thereof,
   b. separating the restriction endonuclease treated DNA sub-fragments according to their length, and
   c. measuring the amount of the DNA preparation identifiable as sub-fragments of the specific desired nucleotide sequence, compared to the total amount of DNA, thereby measuring the purity of the specific desired nucleotide sequence.

2. A method according to claim 1 wherein the DNA is labeled with a radioactive substance and the amount of the radioactive DNA is measured in step c.

3. A method according to claim 1 wherein the separation of step b, is accomplished by gel electrophoresis.

4. A method according to claim 3 wherein the DNA is labeled with a radioactive substance and the amount of radioactive DNA is measured in step c. by autoradiography.

5. A method according to claim 1 wherein the DNA consists essentially of double-stranded DNA.

* * * * *

UNITED STATES PATENT AND TRADEMARK OFFICE
CERTIFICATE OF CORRECTION

PATENT NO. : 4,283,489

DATED : August 11, 1981

INVENTOR(S) : Howard M. Goodman et al

It is certified that error appears in the above—identified patent and that said Letters Patent is hereby corrected as shown below:

On the title page, Item [75] should read:

[75] Inventors: Howard M. Goodman; John Shine;
Peter Horst Seeburg; all of
San Francisco, Calif.

Signed and Sealed this

Second Day of November 1982

[SEAL]

Attest:

GERALD J. MOSSINGHOFF

Attesting Officer     Commissioner of Patents and Trademarks